United States Patent
Kobayashi et al.

(10) Patent No.: US 6,174,489 B1
(45) Date of Patent: *Jan. 16, 2001

(54) METHOD FOR MANUFACTURING A GAS SENSOR UNIT

(75) Inventors: Kiyomi Kobayashi, Kuwana; Naoto Miwa, Tsushima; Toshitaka Saito, Toyohashi; Hiromi Sano, Nagoya; Namitsugu Fujii, Yokkaichi, all of (JP)

(73) Assignee: Denso Corporation, Kariya (JP)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/140,422

(22) Filed: Aug. 26, 1998

Related U.S. Application Data

(63) Continuation-in-part of application No. 08/707,213, filed on Sep. 3, 1996, now abandoned.

(30) Foreign Application Priority Data

| Sep. 8, 1995 | (JP) | 7-248680 |
| Jul. 24, 1996 | (JP) | 8-214379 |
| Feb. 25, 1998 | (JP) | 10-062273 |

(51) Int. Cl.$^7$ .................................................. C07B 33/32
(52) U.S. Cl. ................................. 264/618; 264/619
(58) Field of Search ........................ 264/614, 618, 264/619

(56) References Cited

U.S. PATENT DOCUMENTS

| 4,219,359 | 8/1980 | Miwa et al. | 106/39.5 |
| 4,296,148 | 10/1981 | Friese | 427/125 |
| 4,866,014 | * 9/1989 | Cassidy et al. | 501/103 |
| 5,169,513 | 12/1992 | Mase et al. | 204/429 |
| 5,419,827 | 5/1995 | Nanataki et al. | 204/421 |

FOREIGN PATENT DOCUMENTS

| 2087569 | 5/1982 | (GB) |
| 59-41952 | 10/1984 | (JP) |
| 60-5548 | 2/1985 | (JP) |
| 1-261267 | 10/1989 | (JP) |
| 9-124365 | 5/1997 | (JP) |

* cited by examiner

Primary Examiner—Christopher A. Fiorilla
(74) Attorney, Agent, or Firm—Pillsbury Madison & Sutro

(57) ABSTRACT

A method for manufacturing an oxygen sensor unit of the type which includes at least a shaped body of a solid electrolyte, an inner electrode provided on an inside surface of the shaped body and exposed to a reference gas, an outer electrode provided on an outside surface of the shaped body and exposed to a gas to be measured, and a porous protective layer covering the outer electrode and a portion of the shaped body adjoining to said outer electrode wherein the solid electrolyte is made of a mixture of zirconia and a stabilizer therefor and is constituted of a sintered product of partially stabilized zirconia. The method is characterized in that the partially stabilized, sintered zirconia is obtained according to a high temperature sintering process which includes at least the step of sintering the mixture at a temperature of 1200° C. or over for a duration of 2 to 6 hours wherein a value obtained by integrating a variation in the sintering temperature with the duration in the sintering process is in the range of 300 to 1500° C.·hour.

12 Claims, 7 Drawing Sheets

METHOD FOR MANUFACTURING A GAS SENSOR UNIT

This is a Continuation-in-Part of: National Application Ser. No. 08/707,213 filed Sep. 3, 1996 now abandoned.

BACKGROUND OF THE INVENTION

1. Field of The Invention

This invention relates to a method for manufacturing an oxygen sensor unit which is suitable for use in oxygen sensors of internal combustion engines for automotive vehicles.

2. Description of the Prior Art

For the control of an air-to-fuel ration in internal combustion engines of automotive vehicles, oxygen sensors have been usually used. A typical structure of such a sensor is, for example, shown in FIG. 4 which will be described hereinafter. An oxygen sensor unit incorporated in the oxygen sensor is, for example, of the type which comprises a solid electrolyte body, and a pair of electrodes formed on inner and outer sides of the solid electrolyte, respectively. Moreover, a protective layer is provided to cover the outer electrode therewith at the outer surface thereof so as to protect the outer electrode from a poisonous contaminant in a gas to be measured as shown in FIG. 3. This figure will also be referred to hereinafter.

The solid electrolyte of the oxygen sensor unit has been conventionally made, for example, of a sintered body of zirconia to which a stabilizer is added.

The sintered bodies of the zirconia known in the art can be broadly classified into two groups. One group includes a body made of fully stabilized zirconia which consists essentially of a cubic phase (C phase) alone. The other group includes a body made of partially stabilized zirconia which is constituted mainly of a cubic phase (C phase), a monoclinic phase (M phase) and/or a tetragonal phase (T phase) existing in mingling relation.

The fully stabilized zirconia is one which is stable over a wide temperature range of room temperature (20° C.) to a high temperature of 1000° C. and is unlikely to degrade as time passes. However, this type of zirconia is neither resistant to mechanical shocks such as vibrations, nor resistant to thermal shocks, thus being liable to break. Owing to this deficiency of the fully stabilized zirconia, partially stabilized zirconia sintered bodies have been usually employed as a solid electrolyte in this field of the art.

However, when partially stabilized zirconia is repeatedly subjected to heating and cooling cycles at temperatures between room temperature (20° C.) and a high temperature of 1000° C., phase transformation takes place, as is shown in FIG. 5, between the monoclinic phase (i.e. monoclinic zirconia in the figure) and the tetragonal phase (tetragonal zirconia in FIG. 5).

As will be apparent from FIG. 5, the phase transformation involves a great variation in volume. When using partially stabilized zirconia in an oxygen sensor unit as a solid electrolyte body and subjecting the unit to heating and cooling cycles, this solid electrolyte body may undesirably be cracked or, in the worst case, broken.

In usual practice, a protective layer is formed to protect an outside electrode which is exposed to a gas to be measured as described before. In this condition, if phase transformation accompanying the volumetric variation occurs between the M and T phases of the partially stabilized zirconia sintered body serving as the solid electrolyte, some stress is caused to occur between the solid electrolyte body and the protective layer, with the great possibility that the protective layer suffers cracks and the protective layer separates from the solid electrolyte body or the outer electrode.

SUMMARY OF THE INVENTION

It is accordingly an object of the invention to provide a method for manufacturing an oxygen sensor unit which overcomes the problems of the prior art and wherein a protective layer is prevented from cracking or separation when the unit is repeatedly employed under heating and cooling cycle conditions in internal combustion engines of automotive vehicles and is thus durable.

It is another object of the invention to provide a method for manufacturing an oxygen sensor unit wherein a solid electrolyte body is unlikely to suffer crack or breakage when the unit is placed under heating and cooling cycle conditions.

The above objects can be achieved, according to an embodiment of the invention, by a method for manufacturing an oxygen sensor unit of the type which comprises a shaped body of a solid electrolyte, an inside electrode provided on an inside surface of the shaped body and exposed to a reference gas, an outside electrode provided on an outside side of the shaped body and exposed to a gas to be measured, and a porous protective layer covering the outside electrode and a portion of the shaped body adjoining to the outside electrode wherein the solid electrolyte is made of a mixture of zirconia and a stabilizer therefor and is constituted of partially stabilized, sintered zirconia, the improvement characterized in that the partially stabilized, sintered zirconia is obtained according to a high temperature sintering procedure which comprises the step of sintering the mixture at a temperature of 1200° C. or over for a duration of 2 to 6 hours wherein a value obtained by integrating a variation in the sintering temperature with the duration in the sintering step is 300 to 1500° C.·hour.

PREFERRED EMBODIMENTS OF THE INVENTION

As defined above, the oxygen sensor unit manufactured according to the method of the invention makes use of a solid electrolyte used, which is made of a mixture of zirconia and a stabilizer therefor and is constituted of partially stabilized, sintered zirconia. The stabilized zirconia has such a crystallographic structure that at least a C phase (cubic phase) and an M phase (monoclinic phase) exist in mingling relation, with or without a T phase further existing therein. The method is characterized in that the partially stabilized, sintered zirconia is obtained according to a high temperature sintering procedure which comprises the step of sintering the mixture at a temperature of 1200° C. or over for a duration of 2 to 6 hours wherein a value obtained by integrating a variation in the sintering temperature with the duration in the sintering step is 300 to 1500° C.·hour.

If the sintering temperature in the high temperature sintering process is lower than 1200° C., the sintering does not proceed satisfactorily. The resulting solid electrolyte becomes very low in strength and may suffer breakage under working conditions of an oxygen sensor unit.

Moreover, if the duration in the high temperature sintering process is shorter than 2 hours, the M phase is formed in a greater amount, with the possibility that the protective layer may be cracked or separated from the outer electrode. On the other hand, when the duration is longer than 6 hours, the M phase is formed in a reduced amount, the strength of the resultant solid electrolyte may become lower.

The terms "a value obtained by integration of a variation in the sintering temperature with the duration" used herein means one which is illustrated with reference to FIG. 1.

Figure 1:
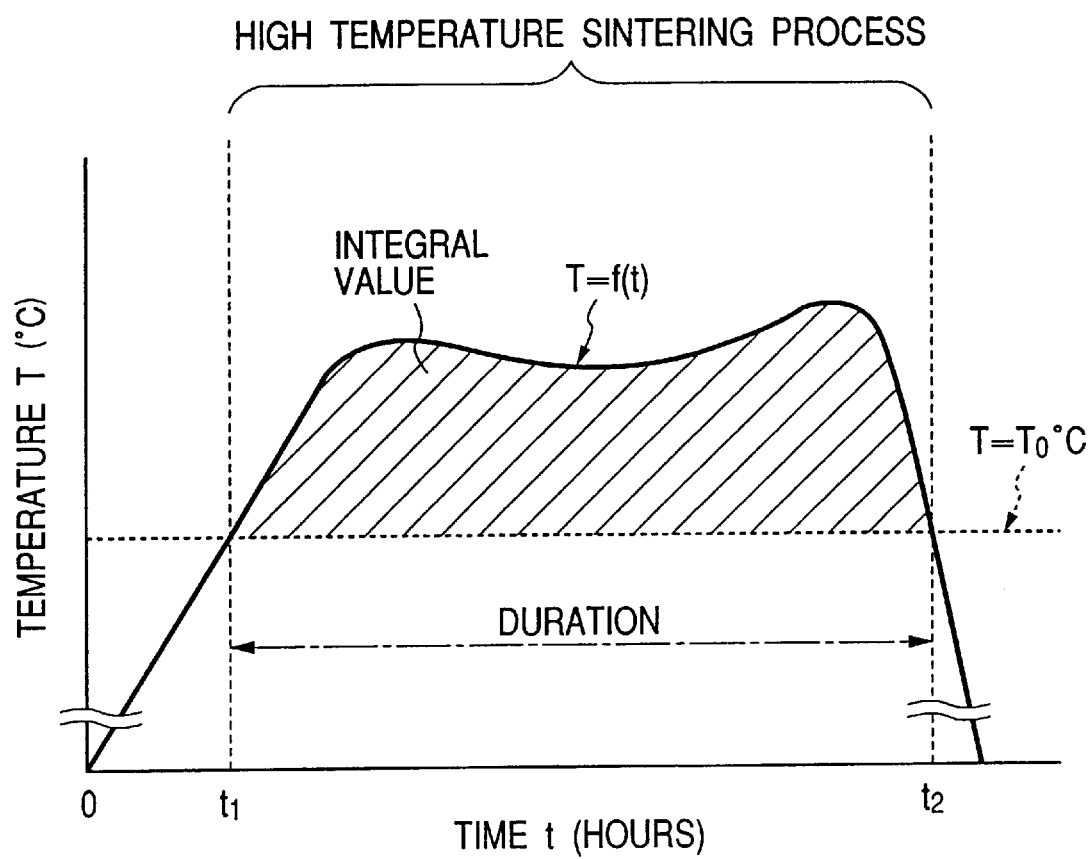
FIG. 1 is a graphical representation of the relationship between the sintering temperature and the duration in a high temperature sintering process according to one embodiment of the invention.

FIG. 1 is a sintering profile wherein a temperature, T, used when a partially stabilized zirconia sintered body is prepared, is taken along the ordinate and the time, t, is taken along the abscissa.

In this sintering profile, when the temperature, T, is $T_o$ or over, a high temperature sintering process is established. In the practice of the invention, $T_0$ is 1200° C. or over as set out hereinbefore. The high temperature sintering process begins from time, $t_1$, and completes at time, $t_2$. More particularly, the duration of the high temperature sintering process ranges $t_2$ to t, and is within a range of 2 to 6 hours in the practice of the invention.

Assuming that the relation between the time and the temperature in the heating profile is expressed as T=f(t), it will be apparent from the figure that $T_o$=f($t_1$) =f($t_2$). The integration value corresponds to an area surrounded by the line of T=$T_0$° C. and the curve T=f(t), which is shaded in the figure.

In the method of manufacturing an oxygen sensor unit according to the invention, the shaded portion amounts to 300 to 1500° C.·hour.

Figure 2:
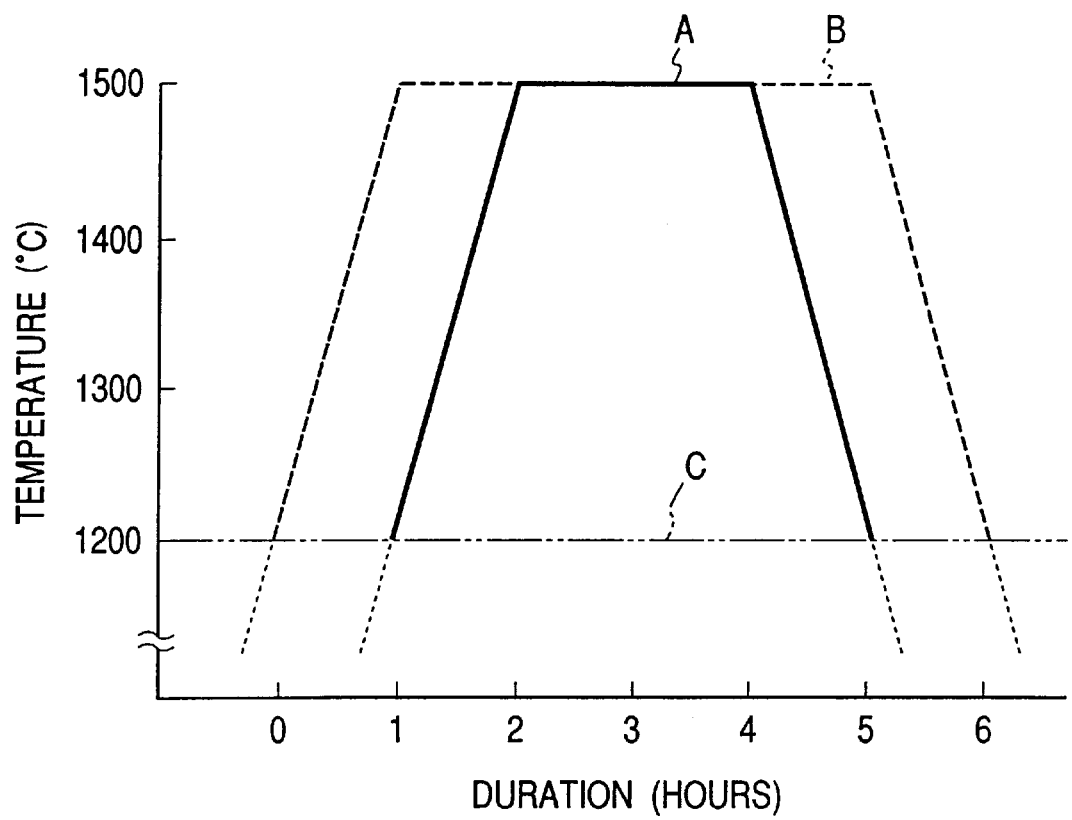
FIG. 2 is a graphical representation illustrating the relationship between the sintering temperature and the duration in a high temperature sintering process according to the one embodiment of the invention.

For instance, as shown in FIG. 2, where the sintering profile of the high temperature sintering process is expressed by solid line A, the integration value corresponds to an area of a trapezoidal form surrounded by the solid line A and the two-dot chain line C. The area of the surrounded portion is represented by 300×(2+4)/2=900° C.·hour (see Embodiment 1 appearing hereinafter).

On the other hand, where the sintering profile of the high temperature sintering process is represented by dotted line B, the integration value corresponds to an area of a trapezoidal form surrounded by the dotted line B and the two-dot chain line C. The area of this portion is such that 300×(6+4)/2=1500° C.·hour.

If the integration value is less than 300° C.·hour, sintering does proceed satisfactorily, resulting in the lowering in strength of the resultant electrolyte body. Alternatively, the M phase may be formed in larger proportions, with the possibility that a protective layer suffers cracks or separation from the solid electrolyte body. On the other hand, when the integration value is greater than 1500° C.·hour, the M phase is formed in proportions smaller than desired, thus leading to the lowering in strength of the resultant solid electrolyte body.

In the practice of the invention, the body of the solid electrolyte should have such a crystallographic structure that is constituted of partially stabilized, sintered zirconia having, at least, the C phase and the M phase with or without the T phase in mingling relation. In the manufacture of an oxygen sensor unit according to the invention, several sintering conditions have been defined in the high temperature sintering process of preparing a sintered body of partially stabilized zirconia which serves as the solid electrolyte body in the oxygen sensor unit.

More particularly, the sintering temperature in the high temperature sintering process is 1200° C. or over, the duration ranges from 2 to 6 hours, and the integration value obtained by integrating a variation in the sintering temperature with the duration ranges from 300 to 1500° C.·hour, under which a mixture of zirconia and a stabilizer therefor is sintered to obtain a sintered body of partially stabilized zirconia When the mixture is sintered under such conditions as mentioned above, the M phase is appropriately formed in the sintered body. As a result, the degree of phase transition between the T and M phases can be reduced with lowering the strength of the solid electrolyte body.

Accordingly, the volumetric change is lessened correspondingly to the reduction in the degree of the phase transition, making it difficult to cause the solid electrolyte body to be cracked or broken as would otherwise occur due to the volumetric variation. Moreover, the lessened volumetric variation in the solid electrolyte body also makes it difficult to cause the protective layer to be cracked and cause the separation between the solid electrolyte body and the outer electrode.

Thus, according to the invention, there can be provided an oxygen sensor unit wherein a solid electrolyte body is unlikely to be cracked or broken, and a protective layer for an outer electrode and the solid electrolyte body is also unlikely to be cracked or separated from the solid electrolyte body, thus the sensor unit being durable.

So far as the high temperature sintering process is carried out under such conditions as defined before in the method of manufacturing an oxygen sensor unit, other steps of the manufacturing method may be performed in any known manner.

For instance, as is particularly shown in Embodiment 1 appearing hereinafter, starting zirconia and a stabilizer therefor may be mixed with binders and shaped in a desired form, after which outer and inner electrodes are printed on the shaped body of the solid electrolyte, followed by sintering.

According to the invention, the sensor unit may be shaped in a so-called cup form wherein a cup-shaped solid electrolyte body is used. Alternatively, the solid electrolyte body may be in the form of a sheet or plate, on which a pair of electrodes are formed on opposite sides thereof.

It is preferred that the sintered body of partially stabilized zirconia is obtained by sintering at a temperature of 1350 to 1500° C. Within this temperature range, the solid electrolyte is sintered adequately to obtain a bending strength, for example, of 18 kgf/mm². If the temperature is lower than 1350° C., sintering may not proceed satisfactorily, with the possibility that the resultant solid electrolyte body is short of mechanical strength. On the contrary, when the sintering temperature exceeds 1500° C., there may not be obtained a solid electrolyte body which has good mechanical strength owing to the excess grain growth.

The partially stabilized zirconia sintered body should preferably have a composition comprising 89 to 97 mole % of zirconia and 3 to 11 mole % of a stabilizer therefor. The solid electrolyte body having such a composition exhibits good oxygen ionic conductivity and satisfactory strength. If the stabilizer is present in amounts less than 3 mole % (i.e. if the content of partially stabilized zirconia is larger than 97 mole %), sintering may not proceed satisfactorily, resulting in the shortage in strength of the solid electrolyte. On the other hand, when the amount of the stabilizer is larger than 11 mole % (i.e. the amount of partially stabilized zirconia is less than 89 mole %), there is the possibility that the solid electrolyte body is not imparted with good strength owing to the excess grain growth.

The stabilizers used in combination with zirconia preferably include yttria, ytterbium oxide, niobium oxide, calcium oxide, magnesium oxide and mixtures thereof. When using these oxides, the resultant solid electrolyte body exhibits good oxygen ionic conductivity along with good strength.

Preferably, the solid electrolyte body should further comprise a sintering aid made of silica and alumina. Silica and alumina are preferably present in the body in amounts of 0.01 to 0.6 parts by weight and from 0.5 to 10 parts by weight based on 100 parts by weight of the solid electrolyte body, respectively. When using silica and alumina in such amounts as defined above, a desired crystallographic structure can be formed in the solid electrolyte with satisfactory strength.

If the amount of silica is less than 0.1 part by weight, sinterability may become so poor that a sintering temperature exceeding 1500° C. may be necessary. In the worst case, the resulting solid electrolyte body is substantially made of C phase, and its strength lowers owing to the excess grain growth.

On the other hand, when the amount exceeds 0.6 parts by weight,. the sintering temperature becomes lower than 1350° C. The resultant solid electrolyte body may be undesirably formed of M phase substantially in whole.

Moreover, when the amount of alumina is less than 0.5 parts by weight, the function as a sintering aid in combination with silica lowers. As a result, the sintering temperature may exceed 1500° C., with the great possibility that the resultant solid electrolyte body lowers in strength owing to the excess grain growth.

On the other hand, when the amount exceeds 10 parts by weight, excess alumina conversely serves as a sintering retarder. Accordingly, good sinterability may not be attained even when the sintering temperature is set at 1500° C. If it is intended to use higher sintering temperatures, excess grain growth take place, leading to the apprehension that the resultant solid electrolyte body considerably lowers in strength.

Boron oxide, borosilicate glass, aluminium silicate and the like may also be used as the sintering aid.

The partially stabilized zirconia sintered body formed according to the method of the invention should preferably meet the following relationship with respect to the ratio in X-ray diffraction intensity between the crystal face of the monoclinic phase (M phase) as expressed by the Miller indices, $I(\bar{1}1\bar{1})$, and the crystal face of the cubic phase (C phase) as expressed by the Miller indices, $I(\bar{1}1\bar{1})$, in the partially stabilized zirconia:

$$0.05 \leq I(11\bar{1})/I(111) \leq 0.25$$

Within this range, the sintered body ensures an oxygen sensor unit which has satisfactory strength imparted thereto.

If the diffraction intensity ratio is less than 0.25, good oxygen ionic conductivity may not be obtained, and an oxygen sensor unit using such an electrolyte body may not work as a sensor in the worst case.

On the other hand, when the diffraction intensity ratio exceeds 0.25, the M phase is formed in larger amounts, and thus, the degree of phase transformation becomes so great that stable output cannot be expected, with the result that the accurate control of an air-to-fuel ratio may not be possible.

Within a temperature range of 20 to 1000° C., the partially stabilized zirconia sintered body should preferably have a maximum difference, $A c x$, between the thermal expansion coefficients determined from the thermal expansion coefficient curves obtained by heating and cooling the body at $1.5 \times 10^{-6}/°$ C. or below.

Figure 6:
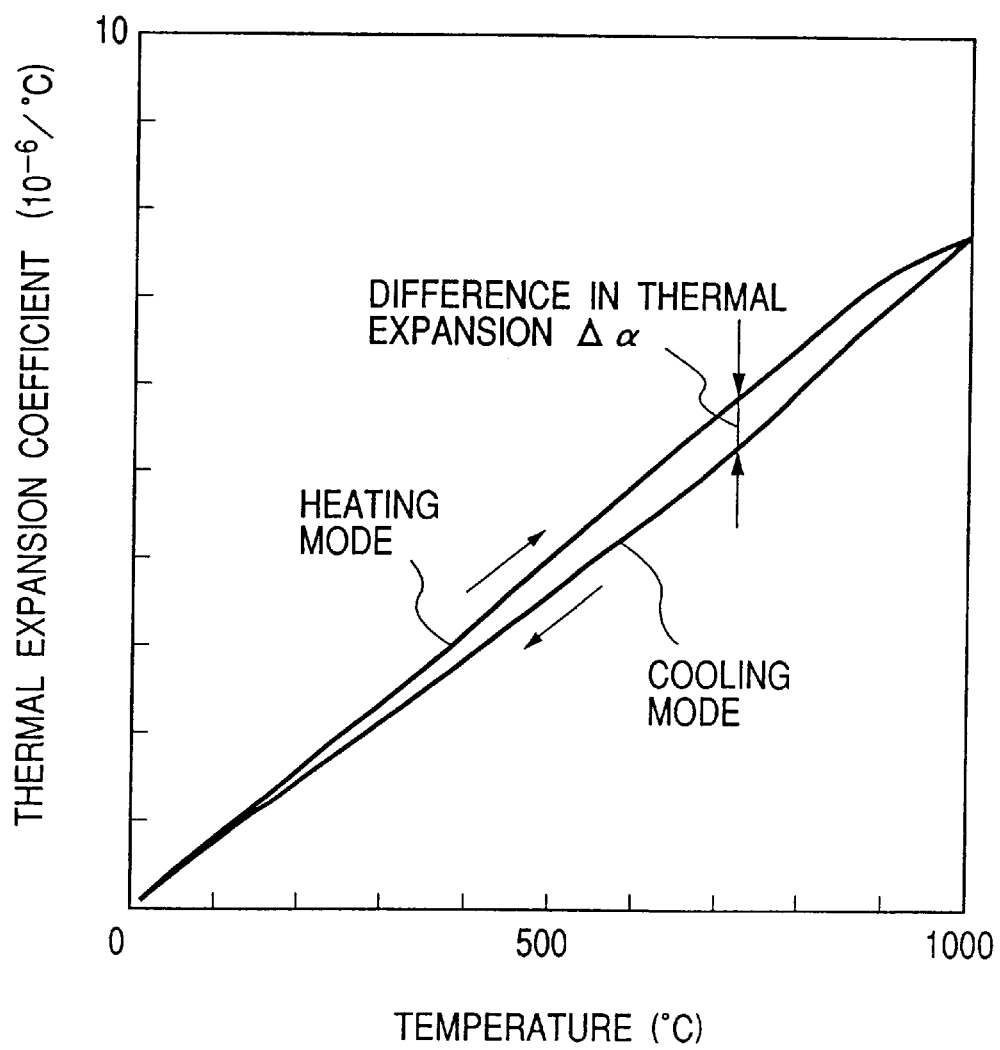
FIG. 6 is a graph showing the relation between the thermal expansion coefficient and the temperature of partially stabilized zirconia according to the one embodiment of the invention.

FIG. 6 shows a thermal expansion curve of the sintered body of partially stabilized zirconia. The thermal expansion coefficient curve means one which is obtained by plotting the linear thermal expansion coefficient of the sintered body along the ordinate and the temperature along the abscissa. As shown in the figure, the thermal expansion curves of the sintered body of partially stabilized zirconia generally differ from each other in the heating and cooling cycles.

Figure 5:
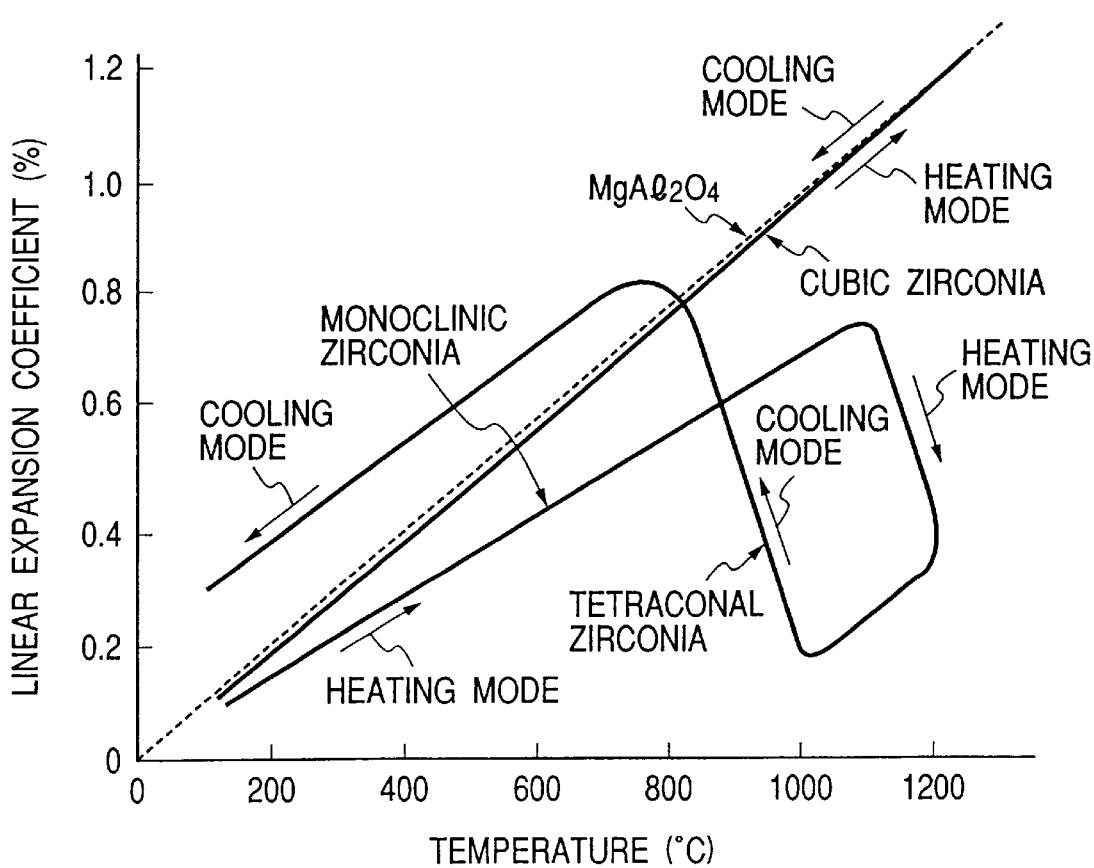
FIG. 5 is a graphical representation showing the relation between the coefficient of linear expansion and the temperature for cubic phase zirconia, monoclinic phase zirconia, tetragonal phase zirconia, and alumina spinnel ($MgAl_2O_4$)

When cubic zirconia and monoclinic zirconia are, respectively, heated from room temperature to 1200° C. and subsequently cooled from 1200° C. to room temperature, variations in the linear expansion coefficient during the heating and cooling cycles are depicted in FIG. 5 for both types of zirconia. From the figure, it will be seen that the linear expansion coefficients of the cubic zirconia under heating and cooling conditions are completely equal to each other over the full temperature range of room temperature to 1200° C., and are in direct proportion to the temperature. This is the behavior of the C phase in the sintered body of partially stabilized zirconia in the course of heating and cooling cycles.

Monoclinic zirconia undergoes phase transition into tetragonal zirconia in the vicinity of a temperature exceeding 1000° C., with its linear thermal expansion decreasing with an increase of temperature over 1000° C. After arriving at a temperature of 1200° C., the zirconia is turned back for cooling, under which tetragonal zirconia undergoes phase transition into monoclinic zirconia at about 1000° C. This brings about the relation between the linear thermal expansion and the temperature, which completely differs from that of tetragonal zirconia. This is the behaviors of the M and T phases in the sintered body of partially stabilized zirconia in the course of heating and cooling cycles.

The sintered body of partially stabilized zirconia obtained according to the method of the invention consists of the C phase and the M phase, and/or optionally the T phase. The respective components, respectively, behave in a manner as shown in FIG. 5, in the heating and cooling cycles. This is why the sintered body shows different thermal expansion curves when heated and cooled, respectively.

The sintered body of partially stabilized zirconia according to the invention preferably has a maximum difference, $\Delta\alpha$, between the thermal expansion coefficients defined above at $1.5 \times 10^{-6}/°$ C. or below within the defined temperature range. When the thermal expansion curves under heating and cooling conditions are compared with each other, their inclinations and shapes have no significant difference.

Accordingly, the difference in cubical expansion and shrinkage between the heating and cooling modes of the solid electrolyte body can be made small. Consequently, the solid electrolyte body is prevented from cracks or breakage.

As will be described hereinafter, the oxygen sensor unit has a protective layer, which may be made, in most cases, of a material different from the solid electrolyte.

In this connection, it is the usual practice to formulate starting compositions for the protective layer and the solid electrolyte body so that they exhibit similar thermal expansion coefficient curves.

However, the sintered body of partially stabilized zirconia has such a thermal expansion coefficient curve as shown in FIG. 6. It has been conventionally very difficult to form a protective layer whose thermal expansion coefficient is invariably substantially equal or similar to that of a solid electrolyte body over low to high temperatures. In this regard, there arises the problem that the protective layer undesirably suffers cracks or separation from other layer or film.

In the practice of the invention, the difference in the thermal expansion coefficient curve between heating and cooling cycles of the sintered body is made so small as defined before, thus making it easy to permit the thermal expansion coefficient of a protective layer to coincide with that of a solid electrolyte body. Hence, the protective layer is reliably prevented from cracks or separation.

Especially, when an oxygen sensor unit is utilized for the control of an air-to-fuel ratio in internal combustion engines of automotives, it is usually exposed to a temperature atmosphere ranging from ambient temperatures (generally at about 20° C. in an atmosphere of an internal combustion engine to be started) to a maximum temperature of an exhaust gas (generally at about 1000° C. in an atmosphere of the internal combustion engine being in operation). The use environment of the oxygen sensor unit can be regarded as cooling and heating cycles in the above temperature range.

Since the maximum difference, $\Delta\alpha$, in the thermal expansion coefficient is defined in a certain range in the practice of the invention, the oxygen sensor unit can be prevented from being damaged on practical use in internal combustion engines of automotives.

If the maximum difference, $\Delta\alpha$, is larger than $1.5\times10^{-6}/°$ C., the preventing effects expected in the present invention may not be appropriately obtained.

When the value of $\Delta\alpha$ is zero, the thermal expansion coefficient curves in the heating and cooling cycles are in coincidence with each other. In this sense, the value of $\Delta\alpha$ is most preferably zero.

In order to realize the defined maximum difference, the protective layer should preferably be made of at least one metal oxide selected from alumina spinnel ($MgAl_2O_4$) and fully stabilized zirconia.

Fully stabilized zirconia is one which is substantially composed of the C phase, with its linear expansion coefficient being substantially equal to that of cubic zirconia as shown in FIG. 5. In the figure, the chain dash indicates a linear expansion coefficient of $MgAl_2O_4$.

As will be apparent from FIGS. 5 and 6, these materials for the protective layer has linear thermal coefficients which are substantially equal to that of the sintered body of partially stabilized zirconia. Accordingly, cracking or separation is unlikely to occur due to the difference in thermal expansion coefficient between the protective layer and the solid electrolyte body.

Preferred embodiments of the invention are described.

Embodiment 1

Reference is now made to FIGS. 1 to 6 to illustrate the method for manufacturing an oxygen sensor unit according to the invention along with its performance being shown in comparison with sensor units for comparison.

Figure 3:
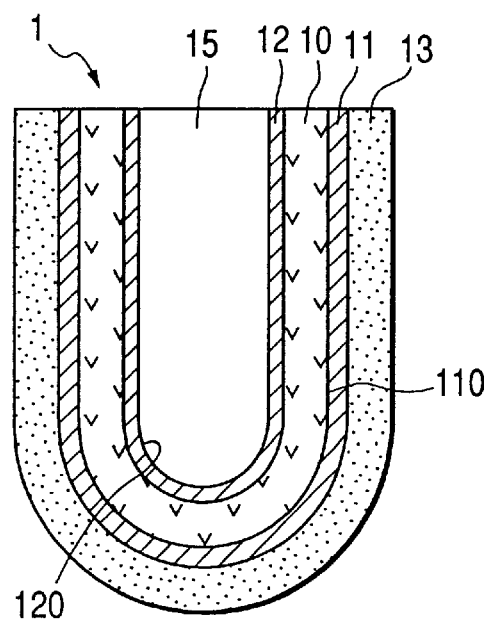
FIG. 3 is a schematic sectional view of an oxygen sensor unit according to the one embodiment of the invention.

FIG. 3 generally shows an oxygen sensor unit 1 which includes a shaped body 10 of a solid electrolyte having an inner space 15 therein. More particularly, the shaped body 15 is in a U shape in section and may be called a cup-shaped body. The sensor unit 1 includes an inner electrode 12 formed on an inner side 120 of the shaped body 10 and exposed to a reference gas, and an outer electrode 11 formed on an outer side 110 of the shaped body 10 and exposed to a gas to be measured. A porous protective layer 13 is provided to cover the outer electrode 11 and the solid electrolyte 10 in the proximity of the outer electrode 11 therewith.

The solid electrolyte body 10 is made of a sintered product of partially stabilized zirconia which is comprised of zirconia and a stabilizer as set out hereinbefore. This sintered product preferably has such a crystallographic structure having, at least, the C phase and the M phase in mingling relation. The sintered product or body of partially stabilized zirconia is formed by high temperature sintering.

As is particularly shown in FIGS., 1 and 2, the sintering temperature in the high temperature sintering step or process for making the sintered body of partially stabilized zirconia is 1200° C. or over, and the duration of the high temperature sintering process ranges from 2 to 6 hours, Moreover, the value of integration obtained by integrating a variation in the sintering temperature in the high temperature sintering process with the duration is in the range of 300 to 1500° C.·hour. If these temperature duration conditions are satisfied, the crystallographic structure may be any one which comprises at least C and M phases. As a matter of course, T phase may further exist in the structure.

The oxygen sensor unit manufactured according to the method of the invention is described in more detail.

Once again, as shown in FIG. 3, the oxygen sensor unit 1 includes the cup-shaped solid electrolyte body 10 which is closed at one end and opened at the other end and which has the inner space 15 as shown. The solid electrolyte body 10 has the outer electrode 110 on the outer surface 110 thereof and the inner electrode 12 formed on the inner surface 120 in the inner space 15.

The outer electrode 11 is further covered with the protective layer 12 so as to protect the solid electrolyte body 10 and the outer electrode 11 from a gas to be measured.

The sintered body of partially stabilized zirconia, of which the solid electrolyte body is formed, has such thermal expansion coefficient curves as shown in FIG. 5. Within a temperature range of from 20 to 1000° C., the hysteresis, $\Delta\alpha$, in the course of heating and cooling cycles is $1.5\times10^{-6}/°$ C. or below.

The outer electrode 11 and the inner electrode 12 are, respectively, made, for example, of platinum, and are formed on the solid electrolyte body 10 by plating, vacuum deposition, baking of a paste.

The protective layer 13 has, aside from the function of protecting the solid electrolyte body 10 and the outer electrode 11, a function as a diffused resistor layer for the oxygen sensor unit 1. This layer 13 is constituted, for example, of $MgAl_2O_4$ spinnel.

The protective layer 12 has a thickness, for example, of 100 $\mu$m and a porosity of 20%, with its thermal expansion coefficient being at $8\times10^{-6}/°$ C.

The oxygen sensor unit 1 arranged in this manner is set in position of an oxygen sensor device. This is particularly described with reference to FIG. 4.

Figure 4:
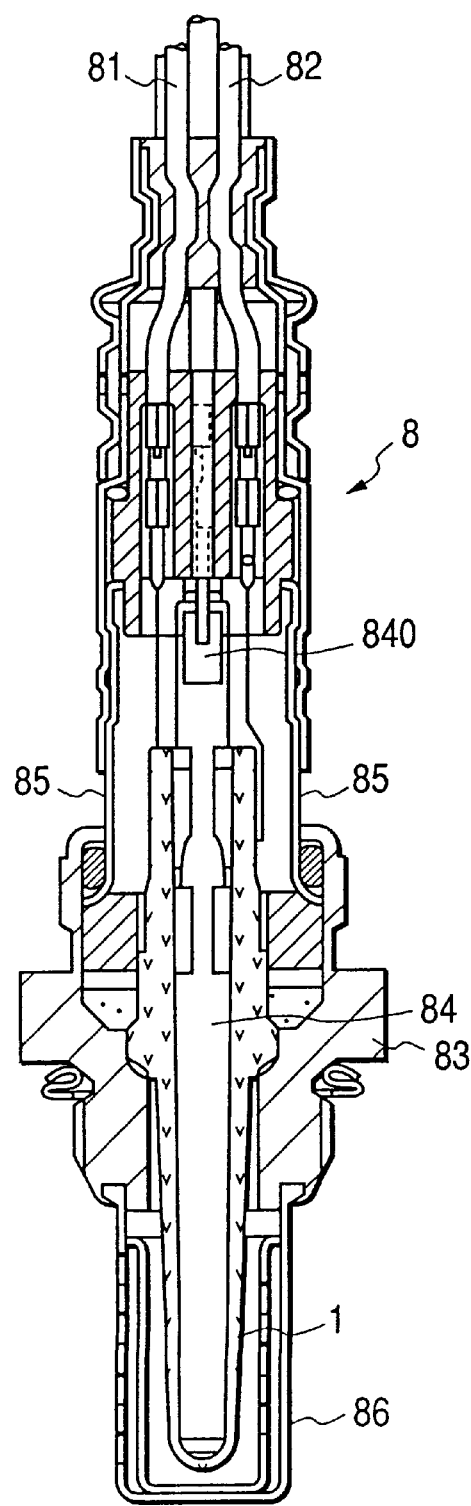
FIG. 4 is schematic sectional view of a typical oxygen sensor which incorporates the oxygen sensor unit shown in FIG. 3.

As shown in FIG. 4, an oxygen sensor device 8 includes a housing 83 in which the oxygen sensor unit 1 is fixed in position. The housing 83 is covered with metallic covers 85, 86 at upper and lower portions thereof.

A heater 84 is inserted into the inner space 15 of the oxygen sensor unit 1 while keeping a given clearance or space between the heater 84 and the inner surface of the oxygen sensor unit 1.

Reference numerals 81, 82, respectively, indicate leads for transmitting a current generated in the solid electrolyte 11 to outside as a signal, and are fixed at the upper portion of the sensor device 8 as shown.

The solid electrolyte body 10 used in this embodiment is more particularly described.

The solid electrolyte body 11 is constituted of an oxygen ion conductive material and a sintering aid as particularly shown in Tables 1-1, 1-2, 2-1 and 2-2 appearing hereinafter.

The oxygen ion conductor material is made, for example, of 95 mole % of zirconia ($ZrO_2$) and 5 mole % of yttria ($Y_2O_3$).

The sintering aid is made of a mixture of alumina and silica, and is added to the ion conductive material in such amounts that 2.0 parts by weight of alumina and 0.2 parts of silica are present per 100 parts by weight of the conductive material.

For the fabrication of the solid electrolyte body 10, zirconia, the stabilizer and the sintering aid are initially formulated, followed by dry or wet mixing and milling by means of a mill such as a vibration mill, a ball mill, a beads mill or the like to obtain a powder mixture.

Thereafter, the powder mixture is molded in the form of a cup, as shown in FIG. 3, according to a molding technique such as rubber press molding, injection molding or the like. The resultant molding is sintered according to a high temperature sintering process using such sintering conditions as indicated by solid line A of FIG. 2. More particularly, the conditions include an overall duration in the high temperature sintering process of 4 hours, an integration value of 900° C.·hour, a maximum sintering temperature of 1500° C., and a duration at the maximum temperature of 2 hours.

The solid electrolyte body 10 obtained in this way is made of a sintered product of partially stabilized zirconia having a crystallographic structure composed of C and M and/or T phases. The ratio between the X-ray diffraction intensities at the crystal face of the monoclinic phase at the Miller indices, $I(11\bar{1})$ in the partially stabilized zirconia and at the crystal face of the cubic phase at the Miller indices, $I(111)$, has been found to be at 0.08.

In addition, the solid electrolyte body 10 exhibits a hysteresis, $\Delta\alpha$, of a thermal expansion curve has been found to be at $0.45 \times 10^{-6}/°$ C.

According to the results of Embodiment 2 described hereinafter, this solid electrolyte body does not suffer any cracks and breakage under working conditions, with the protective layer also suffering any cracks or being free of separation from the solid electrolyte layer. In addition, the solid electrolyte body has strength enough to use in an oxygen sensor unit for controlling an air-to-fuel ratio in automotive engines.

The features and advantages of the method according to this embodiment are described.

In the manufacture of the oxygen sensor unit 1 of Embodiment 1, the sintered product of partially stabilized zirconia used as the solid electrolyte body 10 is obtained according to a high temperature sintering process using severely controlled sintering conditions. More particularly, as shown in FIGS. 1 and 2, the sintering temperature in the process is 1200° C. or over, a duration is 4 hours, and a value of integration obtained by integrating a variation in the sintering temperature with the duration is 900° C.·hour. The sintered product of partially stabilized zirconia is obtained such that the above sintering conditions are satisfied. Moreover, the maximum temperature in the high temperature sintering process is at 1500° C.

In view of the above, it will be seen that the starting composition is sintered at a sintering temperature as low as possible within a minimum time at which the composition is exposed to high temperatures, under which the amount of the M phase being formed in the sintered product can be reduced over that attained in prior art techniques.

As will be apparent from FIG. 5, the monoclinic zirconia undergoes phase transition at temperatures in the neighborhood of 1000° C. and converted to tetragonal zirconia. More particularly, the M phase undergoes phase transition into the T phase while changing its volume.

The sintered product of partially stabilized zirconia obtained in this embodiment has a reduced amount of the M phase contained therein. Accordingly, the solid electrolyte in whole of the embodiment behaves as cubic zirconia as is particularly shown in FIG. 5, with its volumetric change being small.

This is the reason why the solid electrolyte body is unlikely to suffer cracks due to the change in volume thereof, or is unlikely to break.

Further, the protective layer is prevented from being cracked owing to the change in volume of the solid electrolyte body, and the separation of the solid electrolyte body and the outer electrode form the protective layer is unlikely to occur (see Embodiment 2).

Thus, according to this embodiment, there can be provided a method for manufacturing an oxygen sensor unit wherein any crack or breakage is unlikely to occur in the solid electrolyte body, and the protective layer is also unlikely to suffer any crack therein or separate from the solid electrolyte body, thus the sensor unit being durable.

Moreover, the sintered product of partially stabilized zirconia prepared according to the process of this embodiment has a ratio between the X-ray diffraction intensities at the crystal faces defined before at 0.08, which is within a range of $0.05 \leq I(11\bar{1})/I(111) \leq 0.25$. This ensures the fabrication of an oxygen sensor unit having satisfactory strength, and such an oxygen sensor unit is particularly suitable for use in the control of an air-to-fuel ratio of automotive engines as is particularly set out in Embodiment 2.

The solid electrolyte body obtained in this embodiment has a hysteresis, $\Delta\alpha$, of the thermal expansion curve, as is particularly shown in FIG. 6, at $0.45 \times 10^{-6}/°$ C., which is smaller than $1.5 \times 10^{-6}/°$ C. When exposed to cooling and heating cycles, the solid electrolyte body having such a hysteresis value as indicated above does not suffer any adverse influence of thermal stress as would be otherwise exerted thereon. In this regard, the damage of the solid electrolyte body and the separation of the protective layer can be well prevented.

Embodiment 2

In this embodiment, the general procedure of Embodiment 1 for making the sintered product of partially stabilized zirconia is repeated except that slightly different sintering conditions are used as indicated in Tables 1 to 4, thereby obtaining solid electrolyte body samples. These samples are subjected to several tests to compare their performances with one another.

The tests include measurements of a diffraction intensity ratio and a difference in thermal expansion coefficient, $\Delta\alpha$, durability tests described hereinafter wherein it is determined whether or not each solid electrolyte body sample is cracked and broken, and a protective layer associated with the body sample is cracked and separated, and measurement of strength of each solid electrolyte body sample.

The arrangement and the manner of fabrication of sample Nos. 1 to 33 are substantially the same as those described in Embodiment 1. The protective layers of these samples are all formed according to a spray coating technique.

Among sample Nos. 1 to 33, sample Nos. 1 to 27 are those samples obtained through the high temperature sintering process according to the invention, and the other sample Nos. 28 to 33 are for comparison.

The tests are described below one by one.

The diffraction intensity ratio is first described.

Each solid electrolyte sample is milled, and the resultant powder is subjected to measurement of powder X-ray diffraction intensity. Subsequently, the X-ray diffraction intensities at the crystal face of the cubic phase at the Miller indices, $I(111)$, and at the crystal face of the monoclinic phase at the Miller indices, $I(11\bar{1})$ are determined, from which the ratio between $I(11\bar{1})$ and $I(111)$ is calculated.

The value of $\Delta\alpha$ is determined in the following manner. Each solid electrolyte sample is heated from 20° C. to 1200° C. at a rate of 10° C./minute and then cooled down from 1200° C. to 20° C. at a cooling rate of 100° C./minute.

During the heating and cooling cycles of the sample, a linear thermal expansion coefficient of the sample was measured within the above temperature range to obtain thermal expansion curves, as shown in FIG. 6, in the heating and cooling cycles, respectively. From the two thermal expansion curves as shown in FIG. 6, the maximum difference between the thermal expansion coefficients is determined as a value of $\Delta\alpha$ as is particularly shown in FIG. 6. The results are shown in Tables 3 and 4, in which the unit of $\Delta\alpha$ is expressed in terms of $10^{-6}/°$ C.

The cracks in or separation of the protective layer in each sample is observed in the following manner.

Each oxygen sensor unit is subjected to 1000 cooling and heating cycles wherein one cycle includes heating from 20° C. to 1000° C. at a rate of 100° C./minute and cooling from 1000° C. to 20° C. at the same rate.

After completion of the 1000 cooling and heating cycles, the sensor unit is immersed in a colorant solution, followed by observation as to whether or not the solid electrolyte sample is cracked or broken. At the same time, cracks in or separation of the protective layer is also observed.

The observations are made visually, or macroscopically with a magnifier or microscopically with a scanning electron microscope. As a result, where some damage is recognized, such a sample is assessed as "bad" in Tables 3 and 4.

Further, each oxygen sensor unit, which has been subjected to the 100 cooling and heating cycles, is subsequently subjected to a three-point bending test. In this test, when the bending strength is smaller than 18 kgf/mm², the sample is evaluated as "bad", and if the strength is higher than 18 kgf/mm², such a sample is evaluated as "good" in Tables 3 and 4. In the "Cracks in or Breakage of Solid Electrolyte Body", "Cracks in or Separation From Protective Layer" and "Strength" in Tables 3 and 4, when all the measurements are "good", "Overall Evaluation" is assessed as "good". If only one measurement is "bad", the overall evaluation is expressed as "moderate". If two or more measurements are evaluated as "bad", the overall evaluation is made as "bad".

If the overall evaluation is "good", such a sample is considered suitable for special use as an oxygen sensor unit for controlling an air-to-fuel ratio of automotive engines.

As will be apparent from the results in the tables, all the inventive sample Nos. 1 to 27 are assessed as good in all the measurements, and is assessed as good in the column of "Overall Evaluation".

However, sample Nos. 28 to 31 for comparison have diffraction intensity ratios of 0.5 or below. Although they are free of cracks, separation or crack initiation, their strength is so weak that they can be judged as unsuitable for use as an oxygen sensor unit to be employed under severe vibrational conditions such as of automobiles. Thus, the overall evaluation is assessed as "moderate.

Further, sample Nos. 32 and 33 undergo cracking and separation, and are assessed as "bad" in the column of the overall evaluation.

In this way, the oxygen sensor unit manufactured according to the sintering method of the invention comprising a high temperature sintering process is substantially free of any crack in or breakage of its solid electrolyte body, with its protective layer being substantially free of any crack or separation as well. Thus, the oxygen sensor unit has been found to be durable.

TABLE 1-1

| | Solid Electrolyte Body | | | | |
|---|---|---|---|---|---|
| | Oxygen Ion Conductor | | | Sintering Aid | |
| Sample | Zirconia | Stabilizer | | (parts by weight) | |
| No. | mole % | Oxide | mole % | Alumina | Silica |
| 1 | 95 | yttria | 5 | 2 | 0.2 |
| 2 | 95 | yttria | 5 | 2 | 0.2 |
| 3 | 95 | yttria | 5 | 2 | 0.2 |
| 4 | 95 | yttria | 5 | 2 | 0.2 |
| 5 | 95 | yttria | 5 | 2 | 0.2 |
| 6 | 95 | yttria | 5 | 2 | 0.2 |
| 7 | 95 | yttria | 5 | 2 | 0.2 |
| 8 | 95 | yttria | 5 | 2 | 0.2 |
| 9 | 95 | yttria | 5 | 2 | 0.2 |
| 10 | 95 | yttria | 5 | 2 | 0.2 |
| 11 | 95 | yttria | 5 | 2 | 0.2 |
| 12 | 95 | yttria | 5 | 2 | 0.2 |
| 13 | 95 | yttria | 5 | 2 | 0.2 |
| 14 | 97 | yttria | 3 | 5 | 0.6 |
| 15 | 95 | yttria | 5 | 1 | 0.1 |
| 16 | 95 | yttria | 5 | 1 | 0.03 |
| 17 | 95 | yttria | 5 | 0.5 | 0.01 |

TABLE 1-2

| | Sintering Conditions High Temperature Sintering Process | | | | |
|---|---|---|---|---|---|
| Sample No. | Maximum Temperature (° C.) | Duration At Maximum Temperature (Hours) | Duration (hours) | Integration Value (° C. · Hour) | Protective Layer |
| 1 | 1500 | 2 | 4 | 900 | MgAl$_2$O$_4$ |
| 2 | 1500 | 4 | 6 | 1500 | |
| 3 | 1500 | 2 | 6 | 1200 | Spinel |
| 4 | 1500 | 0 | 2 | 300 | |
| 5 | 1500 | 0 | 4 | 600 | |
| 6 | 1450 | 4 | 6 | 1250 | |
| 7 | 1450 | 2 | 4 | 750 | |
| 8 | 1400 | 4 | 6 | 1000 | |
| 9 | 1400 | 2 | 6 | 800 | |
| 10 | 1400 | 2 | 4 | 600 | |
| 11 | 1400 | 0 | 6 | 600 | |
| 12 | 1350 | 4 | 6 | 750 | |
| 13 | 1350 | 3 | 5 | 600 | |
| 14 | 1480 | 2 | 4 | 840 | |
| 15 | 1450 | 2 | 4 | 750 | |
| 16 | 1400 | 2 | 4 | 600 | |
| 17 | 1420 | 3 | 4 | 880 | |

TABLE 2-1

| | Solid Electrolyte Body | | | | |
|---|---|---|---|---|---|
| | Oxygen Ion Conductor | | | Sintering Aid | |
| Sample | Zirconia | Stabilizer | | (parts by weight) | |
| No. | mole % | Oxide | mole % | Alumina | Silica |
| 18 | 95 | yttria | 5 | 2 | 0.05 |
| 19 | 95 | yttria | 5 | 5 | 0.2 |
| 20 | 95 | yttria | 5 | 10 | 0.5 |
| 21 | 93 | yttria | 7 | 2 | 0.3 |
| 22 | 91 | yttria | 9 | 5 | 0.4 |
| 23 | 89 | yttria | 11 | 7 | 0.5 |
| 24 | 95 | Yb$_2$O$_3$ | 5 | 2 | 0.1 |
| 25 | 95 | CaO | 5 | 2 | 0.2 |
| 26 | 95 | yttria | 5 | 2 | 0.2 |

TABLE 2-1-continued

| | Solid Electrolyte Body | | | | |
|---|---|---|---|---|---|
| | Oxygen Ion Conductor | | | Sintering Aid | |
| | Zirconia | Stabilizer | | (parts by weight) | |
| Sample No. | mole % | Oxide | mole % | Alumina | Silica |
| 27 | 95 | yttria | 5 | 2 | 0.2 |
| 28 | 95 | yttria | 5 | 2 | 0.2 |
| 29 | 95 | yttria | 5 | 0.1 | 0.005 |
| 30 | 95 | yttria | 5 | 2 | 0.2 |
| 31 | 97 | yttria | 5 | 2 | 0.2 |
| 32 | 95 | yttria | 5 | 2 | 0.2 |
| 33 | 95 | yttria | 5 | 2 | 0.2 |

TABLE 2-2

| | Sintering Conditions High Temperature Sintering Process | | | | |
|---|---|---|---|---|---|
| Sample No. | Maximum Temperature (° C.) | Duration At Maximum Temperature (Hours) | Duration (hours) | Integration Value (° C. · Hour) | Protective Layer |
| 18 | 1450 | 2 | 4 | 600 | MgAl$_2$O$_4$ |
| 19 | 1450 | 2 | 4 | 750 | |
| 20 | 1500 | 4 | 6 | 1500 | Spinel |
| 21 | 1450 | 2 | 4 | 600 | |
| 22 | 1400 | 4 | 6 | 1000 | |
| 23 | 1350 | 2 | 4 | 600 | |
| 24 | 1450 | 2 | 4 | 600 | |
| 25 | 1450 | 2 | 4 | 600 | |
| 26 | 1400 | 4 | 6 | 1000 | Alumina |
| 27 | 1400 | 4 | 6 | 1000 | Zirconia |
| 28 | 1550 | 4 | 6 | 1750 | MgAl$_2$O$_4$ |
| 29 | 1550 | 3 | 6 | 1575 | |
| 30 | 1500 | 6 | 8 | 2100 | Spinel |
| 31 | 1500 | 4 | 8 | 1500 | |
| 32 | 1330 | 6 | 8 | 610 | |
| 33 | 1300 | 0 | 4 | 200 | |

TABLE 3

| Sample No. | Diffraction Intensity Ratio | Δα | Cracks in or Breakage of Solid Electrolyte Body | Cracks in or Separation of Protective Layer | Bending Strength | Overall Evaluation |
|---|---|---|---|---|---|---|
| 1 | 0.08 | 0.45 | good | good | good | good |
| 2 | 0.06 | 0.4 | good | good | good | good |
| 3 | 0.07 | 0.43 | good | good | good | good |
| 4 | 0.09 | 0.48 | good | good | good | good |
| 5 | 0.12 | 0.57 | good | good | good | good |
| 6 | 0.13 | 0.6 | good | good | good | good |
| 7 | 0.14 | 0.65 | good | good | good | good |
| 8 | 0.14 | 0.63 | good | good | good | good |
| 9 | 0.13 | 0.58 | good | good | good | good |
| 10 | 0.15 | 0.67 | good | good | good | good |
| 11 | 0.18 | 0.85 | good | good | good | good |
| 12 | 0.18 | 0.8 | good | good | good | good |
| 13 | 0.22 | 1.3 | good | good | good | good |
| 14 | 0.06 | 0.42 | good | good | good | good |
| 15 | 0.15 | 0.7 | good | good | good | good |
| 16 | 0.15 | 0.66 | good | good | good | good |
| 17 | 0.12 | 0.54 | good | good | good | good |

TABLE 4

| Sample No. | Diffraction Intensity Ratio | Δα | Cracks in or Breakage of Solid Electrolyte Body | Cracks in or Separation of Protective Layer | Bending Strength | Overall Evaluation |
|---|---|---|---|---|---|---|
| 18 | 0.16 | 0.72 | good | good | good | good |
| 19 | 0.01 | 0.51 | good | good | good | good |
| 20 | 0.05 | 0.38 | good | good | good | good |
| 21 | 0.17 | 0.7 | good | good | good | good |
| 22 | 0.21 | 0.98 | good | good | good | good |
| 23 | 0.25 | 1.5 | good | good | good | good |
| 24 | 0.14 | 0.65 | good | good | good | good |
| 25 | 0.17 | 0.75 | good | good | good | good |
| 26 | 0.14 | 0.65 | good | good | good | good |
| 27 | 0.14 | 0.6 | good | good | good | good |
| 28 | 0.01 | 0.15 | bad | good | bad | moderate |
| 29 | 0.03 | 0.3 | good | good | bad | moderate |
| 30 | 0.02 | 0.2 | good | good | bad | moderate |
| 31 | 0.04 | 0.35 | good | good | bad | moderate |
| 32 | 0.27 | 1.8 | bad | bad | good | bad |
| 33 | 0.32 | 2.2 | bad | bad | bad | bad |

Embodiment 3

Another embodiment of the invention is described with reference to FIGS. 7 and 8. In these figures, there is shown an oxygen sensor unit 19 having a second protective layer 16 formed on the protective layer 13.

Figure 7:
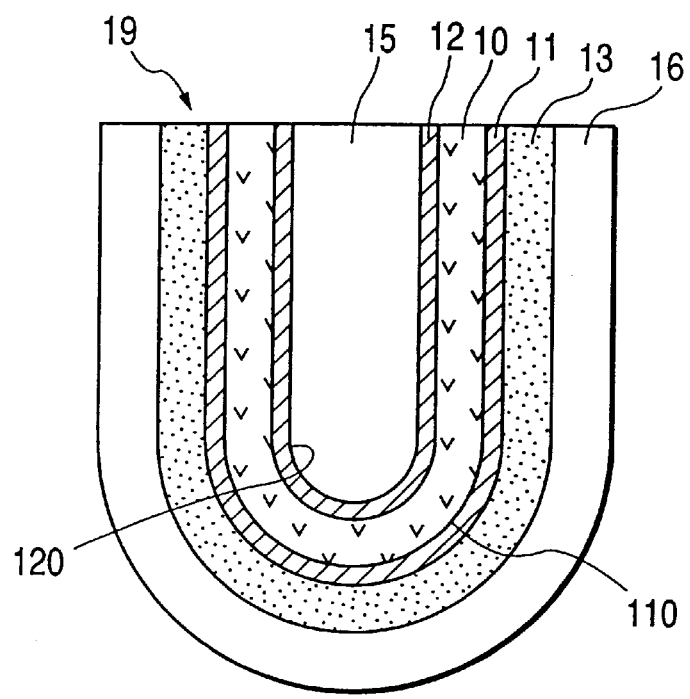
FIG. 7 is a schematic sectional view illustrating an oxygen sensor unit according to another embodiment of the invention.

More particularly, as shown in FIG. 7, the oxygen sensor unit 19 of this embodiment is provided with the second protective layer 16 on the surface of the protective layer 13 in order to enhance the trapping effect of harmful components contained in a gas to be measured. The second protective layer 16 is made, for example, of alumina with its thickness at 120 μm and porosity at 20 to 50%.

For the formation of the second protective layer 16, a slurry containing alumina is prepared and coated onto the surface of the protective layer 13 by dipping, followed by thermal treatment of the solid electrolyte body in whole. In this manner, the oxygen sensor unit 19 having the second protective layer 1 is formed.

Figure 8:
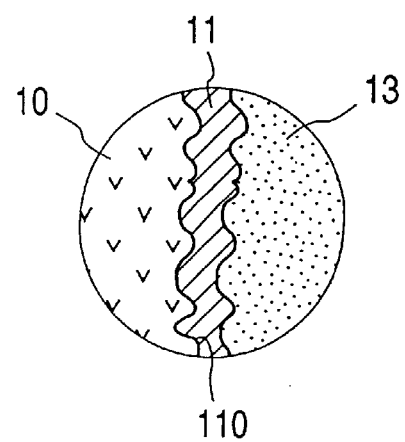
FIG. 8 is a schematic enlarged view showing an essential part of the oxygen sensor unit shown in FIG. 7.

It will be noted that, as is particularly shown in FIG. 8, the shaped solid electrolyte body 10 of the oxygen sensor unit 19 is formed with irregularities on the outside surface 110 of the solid electrolyte body 10. The outer electrode 11 and the protective layer 13 are successively formed as shown.

The other arrangement is same as that of Embodiment 1.

The irregularities, which are formed on the outer surface of the solid electrolyte body 10, ensures stronger bonding strength between the solid electrolyte body 10 and the outer electrode 11 or the protective layer 13. In this regard, the unit 19 is improved over the oxygen sensor unit of Embodiment 1.

Embodiment 4

Figure 9:
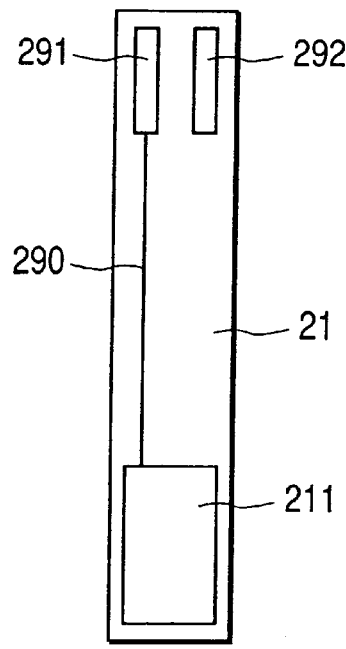
FIG. 9 is a schematic plan view showing a body of a solid electrolyte in an oxygen sensor unit according to a further embodiment of the invention.
Figure 10:
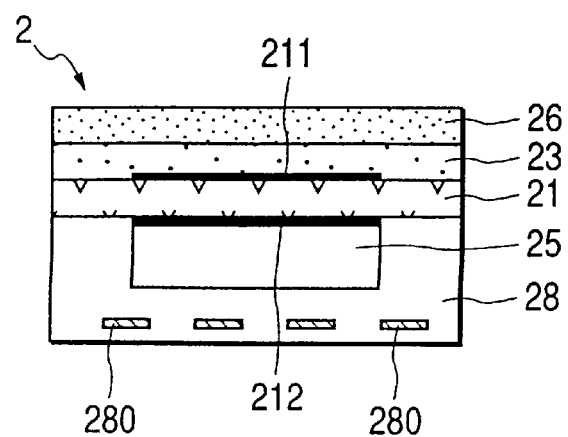
FIG. 10 is a schematic sectional view showing an oxygen sensor unit of FIG. 9.

This embodiment illustrates a built-up oxygen sensor unit 2 shown in FIGS. 9 and 10.

As shown in FIG. 10, the oxygen sensor unit 2 has a solid electrolyte sheet 21 having outer and inner electrodes 211 and 212 on opposite sides of the sheet 21 as shown. The outer electrode 211 is covered with a first protective layer 23, which is, in turn, covered with a second protective layer 26. At the side where the inner electrode 212 is provided, a substrate 28 of a U shape section capable of providing an air feed duct 25 in association with the inner electrode 212.

The substrate 28 is usually made of alumina and is shaped according to any known molding procedures including press molding, injection molding, sheet molding and the like. The substrate 28 is built in with heat units 280 as shown.

The outer electrode 211 is electrically connected to a terminal 291 via a lead 290 as shown in FIG. 9. Likewise, the inner electrode 212 is electrically connected to a terminal 292 via a lead (not shown). A sensor output is taken out to outside through the terminals 291, 292.

The other arrangement is similar to that of Embodiment 1.

What is claimed is:

1. A method of manufacturing a gas sensor unit which comprises a solid electrolyte shaped body having inner and outer surfaces, an inner electrode provided on the inner surface of the shaped body and exposed to a reference gas, an outer electrode provided on an outer surface of the shaped body and exposed to a gas to be measured, and a porous protective layer covering the outer electrode and a portion of the shaped body adjoining the outer electrode, said method comprising forming the solid electrolyte shaped body by a high temperature sintering process comprising:

sintering a mixture comprising zirconia, at least one stabilizer thereof, and a sintering aid comprising silica and alumina, wherein the silica is present in an amount of from 0.01 to 0.6 parts by weight and the alumina is present in an amount of from 0.5 to 10 parts by weight, each based per 100 parts by weight of the solid electrolyte, at a sintering temperature of at least 1200° C. for a sintering period of from 4 to 6 hours to form a partially stabilized zirconia sintered product, wherein a value obtained by integrating a variation in the sintering temperature with the sintering period is in a range of from 300 to 1500° C.·hr, and wherein the sintered product has a crystallographic structure comprising a monoclinic phase and a cubic phase, wherein the sintered product has a ratio of X-ray diffraction intensities at a crystal face of the monoclinic phase as expressed by Miller indices $I(11\bar{1})$ to a crystal phase of the cubic phase as expressed by Miller indices $I(111)$ in the partially stabilized zirconia in a range of from not less than 0.05 to not more than 0.25.

2. The method of claim 1, wherein the value obtained by integrating a variation in the sintering temperature with the sintering period is in a range of from 600 to 1500° C.·hr.

3. The method of claim 1, wherein the sintering temperature is in arrange of from 1350° C. to 1500° C.

4. The method of claim 1, wherein the sintered product comprises 89 mol % to 97 mol % of zironia, with the remainder being the stabilizer.

5. The method of claim 4, wherein the stabilizer consists of essentially of at least one member selected from the group consisting of yttria, ytterbium oxide, niobium oxide, calcium oxide, and magnesium oxide.

6. The method of claim 1, wherein the protective layer comprises a metal oxide selected from the group consisting of alumina spinnel ($MgAl_2O_4$) and fully stabilized zirconia.

7. A method of manufacturing a gas sensor unit which comprises a solid electrolyte shaped body having inner and outer surfaces, an inner electrode provided on the inner surface of the shaped body and exposed to a reference gas, an outer electrode provided on an outer surface of the shaped body and exposed to a gas to be measured, and a porous protective layer covering the outer electrode and a portion of the shaped body adjoining the outer electrode, said method comprising forming the solid electrolyte shaped body by a high temperature sintering process comprising:

sintering a mixture comprising zirconia, at least one stabilizer thereof, and a sintering aid comprising silica and alumina, wherein the silica is present in an amount of from 0.01 to 0.6 parts by weight and the alumina is present in an amount of from 0.5 to 10 parts by weight, each based per 100 parts by weight of the solid electrolyte, at a sintering temperature of at least 1200° C. for a sintering period of from 4 to 6 hours to form a partially stabilized zirconia sintered product, wherein a value obtained by integrating a variation in the sintering temperature with the sintering period is in a range of from 300 to 1500° C.·hour, wherein the sintered product has a crystallographic structure comprising a monoclinic phase and a cubic phase, and wherein the sintered product has a maximum difference $\Delta\alpha$ between thermal coefficients thereof in thermal expansion curves in the course of heating and cooling modes of the sintered product in a temperature range of 20° C. to 1000° C. at $1.5 \times 10^{-6}$/° C. or below.

8. The method of claim 7, wherein the value obtained by integrating a variation in the sintering temperature with the sintering period is in a range of from 600 to 1500° C.·hr.

9. The method of claim 7, wherein the sintering temperature is in a range of from 1350° C. to 1500° C.

10. The method of claim 7, wherein the sintered product comprises 89 mol % to 97 mol % of zironia, with the remainder being the stabilizer.

11. The method of claim 10, wherein the stabilizer consists of essentially of at least one member selected from the group consisting of yttria, ytterbium oxide, niobium oxide, calcium oxide, and magnesium oxide.

12. The method of claim 7, wherein the protective layer comprises a metal oxide selected from the group consisting of alumina spinel ($MgAl_2O_4$) and fully stabilized zirconia.

* * * * *

UNITED STATES PATENT AND TRADEMARK OFFICE
CERTIFICATE OF CORRECTION

PATENT NO.    : 6,174,489 B1
DATED         : January 16, 2001
INVENTOR(S)   : Kobayashi et al.

Page 1 of 1

It is certified that error appears in the above-identified patent and that said Letters Patent is hereby corrected as shown below:

Title page,
Please correct to read as follows:

Item [30]    Foreign Application Priority Data

Sep. 1, 1995  (JP) ............................................ 7-248680
Jul. 24, 1996 (JP) ............................................ 8-214379
Feb. 25, 1998 (JP) ............................................10-062273

Signed and Sealed this

Sixteenth Day of October, 2001

Attest:

NICHOLAS P. GODICI
Attesting Officer   Acting Director of the United States Patent and Trademark Office